US012686671B2

(12) United States Patent
Kim et al.

(10) Patent No.: US 12,686,671 B2

(45) Date of Patent: Jul. 21, 2026

(54) METHOD FOR PREPARING SPHINGOSINE-1-PHOSPHATE RECEPTOR AGONIST

(71) Applicant: LG CHEM, LTD., Seoul (KR)

(72) Inventors: Sung Wook Kim, Daejeon (KR); Ki Dae Kim, Daejeon (KR); Soo Min Lee, Daejeon (KR); Doo Sup Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 277 days.

(21) Appl. No.: 18/555,233

(22) PCT Filed: Apr. 14, 2022

(86) PCT No.: PCT/KR2022/005405

§ 371 (c)(1), (2) Date: Oct. 12, 2023

(87) PCT Pub. No.: WO2022/220613

PCT Pub. Date: Oct. 20, 2022

(65) Prior Publication Data

US 2024/0228461 A1 Jul. 11, 2024

(30) Foreign Application Priority Data

Apr. 14, 2021 (KR) ........................ 10-2021-0048768

(51) Int. Cl.
*C07D 401/12* (2006.01)
*C07D 231/56* (2006.01)

(52) U.S. Cl.
CPC ......... *C07D 401/12* (2013.01); *C07D 231/56* (2013.01)

(58) Field of Classification Search
None
See application file for complete search history.

(56) References Cited

U.S. PATENT DOCUMENTS

| | | | | |
|---|---|---|---|---|
| 8,193,378 | B2 * | 6/2012 | Harada | A61P 35/00 549/407 |
| 9,540,362 | B2 | 1/2017 | Paek et al. | |
| 11,947,259 | B2 * | 4/2024 | Zhao | G03F 7/0007 |
| 2007/0167425 | A1 | 7/2007 | Nakade et al. | |
| 2009/0275554 | A1 | 11/2009 | Habashita et al. | |
| 2010/0160357 | A1 | 6/2010 | Caldwell et al. | |
| 2011/0020324 | A1 | 1/2011 | Nakade et al. | |
| 2011/0105432 | A1 | 5/2011 | Habashita et al. | |
| 2011/0152241 | A1 | 6/2011 | Nguyen et al. | |
| 2011/0212925 | A1 | 9/2011 | Nguyen et al. | |
| 2011/0230463 | A1 | 9/2011 | Harada et al. | |
| 2012/0178735 | A1 | 7/2012 | Harada et al. | |
| 2014/0023636 | A1 | 1/2014 | Habashita et al. | |
| 2014/0107075 | A1 | 4/2014 | Heidelbaugh et al. | |
| 2014/0288034 | A1 | 9/2014 | Nakade et al. | |
| 2015/0284405 | A1 | 10/2015 | Trzupek et al. | |
| 2015/0376173 | A1 | 12/2015 | Paek et al. | |
| 2016/0347760 | A1 | 12/2016 | Trzupek et al. | |
| 2018/0127432 | A1 | 5/2018 | Trzupek et al. | |
| 2019/0270751 | A1 | 9/2019 | Trzupek et al. | |
| 2020/0377511 | A1 | 12/2020 | Trzupek et al. | |
| 2023/0047472 | A1 * | 2/2023 | Paek | C07D 405/12 |
| 2023/0330077 | A1 * | 10/2023 | Kim | A61P 17/00 |
| 2024/0002322 | A1 * | 1/2024 | Kim | C07C 67/29 |
| 2024/0217935 | A1 * | 7/2024 | Kim | C07D 231/56 |
| 2024/0228441 | A1 * | 7/2024 | Kim | C07D 231/56 |
| 2024/0228461 | A1 * | 7/2024 | Kim | C07D 231/56 |

FOREIGN PATENT DOCUMENTS

| | | | |
|---|---|---|---|
| AU | 2005314938 | A1 | 6/2006 |
| CN | 101407471 | A | 4/2009 |
| CN | 102239164 | A | 11/2011 |
| CN | 102712607 | A | 10/2012 |
| CN | 105051037 | A | 11/2015 |
| EP | 1826197 | A1 | 8/2007 |
| KR | 10-2011-0140139 | A | 12/2011 |
| KR | 10-2014-0104376 | A | 8/2014 |
| KR | 10-1589332 | B1 | 1/2016 |
| TW | 201028142 | A | 8/2010 |
| TW | I433830 | B | 4/2014 |
| TW | I593683 | B | 8/2017 |
| WO | 2014-129796 | A1 | 8/2014 |

OTHER PUBLICATIONS

International Search Report issued for International Application No. PCT/KR2022/005405 on Jul. 22, 2022, 7 pages.

Mondal, Rina et al., "Recent Applications of Potassium Carbonate in Organic Synthesis," Organic Preparations and Procedures International: The New Journal for Organic Synthesis, 2014, 46(5), 391-434, XP093188201.

Extended European search report issued on Aug. 12, 2024 for the corresponding European patent application No. 22788468.1. 7 pages.

Marciniak et al., "An update on sphingosine-1-phosphate receptor 1 modulators." Bioorg Med Chem Lett. (2018) 28.23-24: 3585-3591.

* cited by examiner

*Primary Examiner* — Andrew D Kosar

(74) *Attorney, Agent, or Firm* — ROTHWELL, FIGG, ERNST & MANBECK, P.C.

(57) ABSTRACT

The present invention relates to a novel method for preparing a compound of chemical Formula 7, or a salt thereof, which is disclosed in the present specification and can be effectively used as a sphingosine-1-phosphate receptor agonist.

9 Claims, 1 Drawing Sheet

METHOD FOR PREPARING SPHINGOSINE-1-PHOSPHATE RECEPTOR AGONIST

CROSS-REFERENCE TO RELATED APPLICATIONS

The present application is a 35 U.S.C. § 371 National Phase Entry Application from PCT/KR2022/005405, filed on Apr. 14, 2022, which claims the benefit of priority based on Korean Patent Application No. 10-2021-0048768, filed on Apr. 14, 2021, the entire disclosures of which are incorporated by reference herein as part of the specification.

TECHNICAL FIELD

The present invention relates to a novel preparation method for synthesizing a sphingosine-1-phosphate receptor agonist.

BACKGROUND

Sphingosine-1-phosphate (S1P) is produced via an intracellular ceramide pathway, in which ceramide is the starting material. Ceramide is produced via two pathways, the first of which is de novo biosynthetic pathway. Ceramide is also produced by the degradation of sphingomyelin, a cell membrane constituent, in a cell. The S1P level in each tissue is controlled by two biosynthetic sphingosine kinases (SphKs) and two biodegradable S1P phosphatases (S1P lyase and lysophospholipid phosphatases). S1P, produced via phosphorylation of sphingosine by sphingosine kinase, is known to mediate various cellular responses, such as cell proliferation, cytoskeletal organization and migration, adherence- and tight junction assembly, and morphogenesis. S1P exists as a combined form with other plasma proteins, including albumin, at a high level (100-1000 nM) in plasma, while it is at a low level in tissues.

S1P binds with the S1P receptor, a G-protein coupled receptor, to show various biological functions. As S1P receptor sub-types, S1P1-S1P5 are known up to now and are named endothelial differentiation gene (EDG) receptors 1, 5, 3, 6, and 8, respectively. The S1P receptors are known to be involved in various biological functions such as leukocyte recirculation, neural cell proliferation, morphological changes, migration, endothelial function, vasoregulation, and cardiovascular development.

In recent years, many studies have found that the S1P signaling process via these receptors plays an important role in a series of responses related to multiple sclerosis, including inflammation response and the repair process, and a non-selective S1P1 agonist has been recently and actually approved as a therapeutic agent for multiple sclerosis. The S1P receptors are extensively expressed in many cells related to the induction of multiple sclerosis. Especially, the S1P1 receptor plays a very important role in the immune system. The S1P1 receptor is mainly expressed on the surface of lymphocytes such as T cells and B cells and responds to S1P, resulting in involvement in recirculation of lymphocytes. In normal conditions, the S1P concentration is higher in body fluid than in lymphoid tissue, and therefore lymphocytes leave lymphoid tissue by the difference of S1P concentration to circulate along efferent lymph. However, when the S1P1 receptor in lymphocytes is down-regulated by an S1P1 agonist, the egress of lymphocytes from lymphoid tissue does not occur, resulting in reduced infiltration of autoaggressive lymphocytes, which cause inflammation and tissue damage in the central nervous system (CNS). As a result, a therapeutic effect on multiple sclerosis is obtained. Fingolimod, a non-selective S1P1 agonist, has been approved as an oral medication for treating multiple sclerosis. When it binds to the S1P1 receptor and is activated, the receptor becomes degraded or internalized from the surface of lymphocytes. Thus, fingolimod acts as a functional S1P1 antagonist paradoxically.

Concerning such an S1P receptor agonist, Korean Unexamined Publication No. 10-2014-0104376 discloses a novel compound of Formula 1, which is effective as an S1P receptor agonist:

[Formula 1]

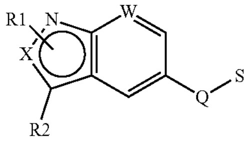

wherein

X is C or N,

R1 is H or a substitutable alkyl,

R2 is H, a substitutable alkyl, a halogen, CN, $CF_3$, or $COCF_3$,

W is C, N, C-alkoxy, C-halogen, or C—CN,

Q is $CH_2O$ or

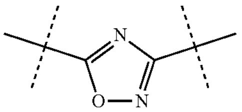

,

S is selected from among the following moieties:

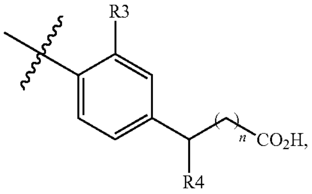

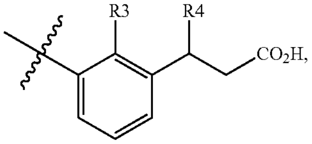

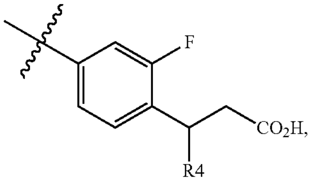

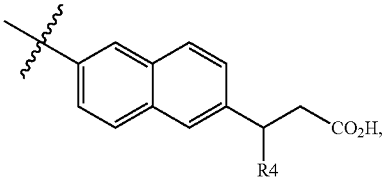

-continued
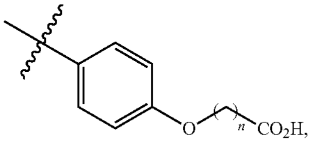
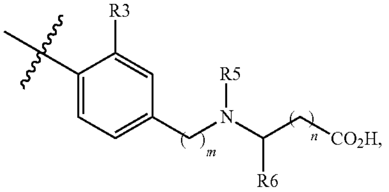
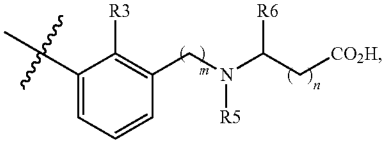
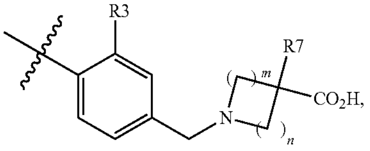
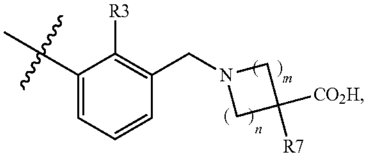
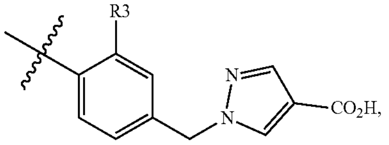
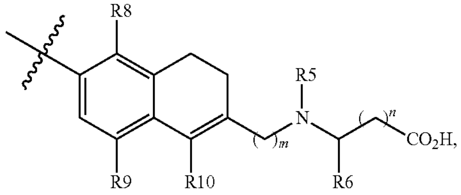
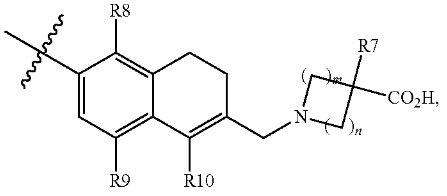
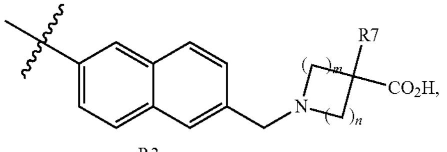
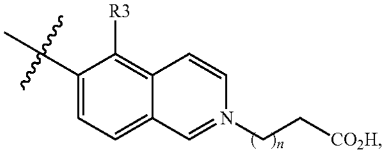
-continued
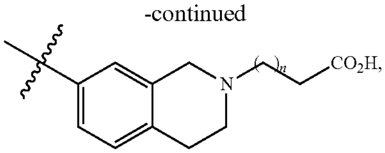
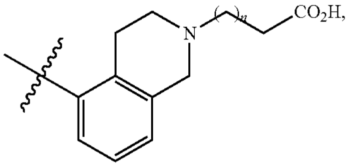
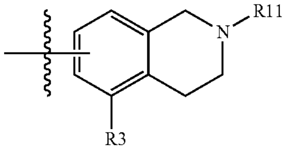
and
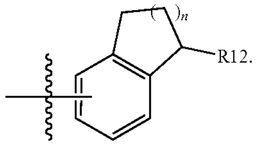
In the above structural formulae,
m and n are 0, 1, 2, or 3,
R3 to R10 are each H, an alkyl, a halogen, a halogenoalkyl, or an alkoxy alkyl,
R11 is H,
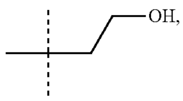
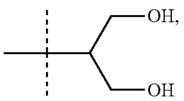
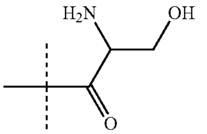
or
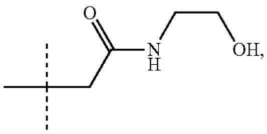
R12 is OH, $NH_2$,
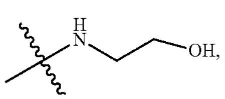
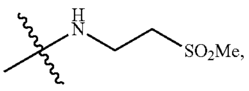
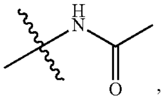
,
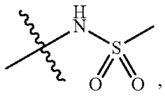
,
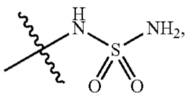
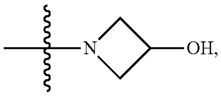
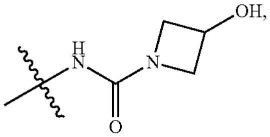
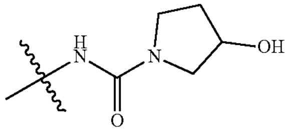
or -continued

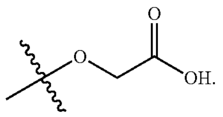

In a specific example of the above document, the preparation of 1-[1-chloro-6-(3-chloro-1-isopropyl-1H-indazol-5-ylmethoxy)-3,4-dihydro-naphthalen-2-ylmethyl]piperidine-4-carboxylic acid according to scheme 1 below is disclosed (in scheme 1, "SG35" refers to "1-chloro-6-hydroxy-3,4-dihydro-naphthalene-2-carbaldehyde").

[Scheme 1]

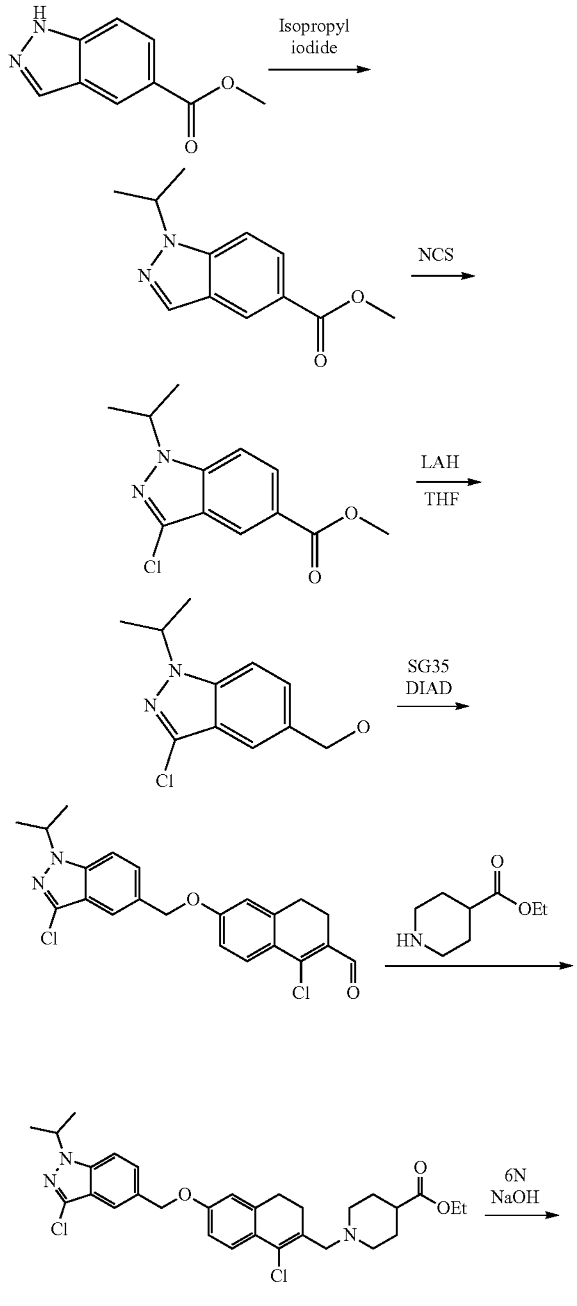

-continued

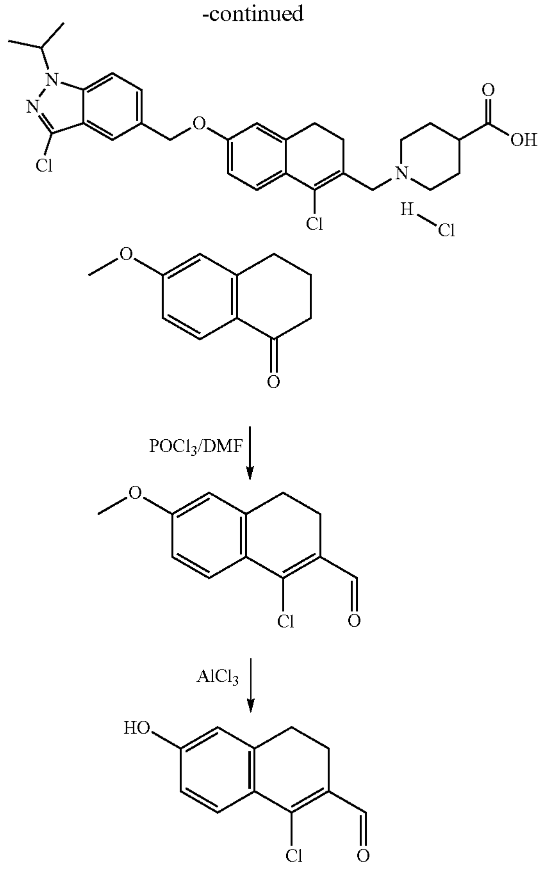

SG35

In scheme 1 above, a step for preparing 1-chloro-6-(3-chloro-1-isopropyl-1H-indazol-5-ylmethoxy)-3,4-dihydro-naphthalen-2-carbaldehyde is described in more detail as follows.

(1-1) Synthesis of (3-chloro-1-isopropyl-1H-indazol-5-yl)-methanol

1H-Indazole-5-carboxylic acid methyl ester was dissolved in dimethylformamide, and isopropyl iodide and sodium hydride were slowly added dropwise at 0° C., followed by stirring at 50° C. for 8 hours. 1 N hydrochloric acid solution was added, and extraction with ethyl acetate was carried out. The extract was washed with brine, dried with anhydrous magnesium sulfate and filtered. The filtrate was distilled under reduced pressure. Separation by column chromatography gave 1-isopropyl-1H-indazole-5-carboxylic acid methyl ester.

1-isopropyl-1H-indazole-5-carboxylic acid methyl ester obtained above was dissolved in dimethylformamide, and N-chlorosuccinimide (NCS) was added dropwise, followed by stirring at room temperature for 18 hours. Water was added, and extraction with ethyl acetate was carried out. The extract was washed with brine, dried with anhydrous magnesium sulfate and filtered. The filtrate was distilled under reduced pressure. The residue was separated by column chromatography to obtain 3-chloro-1-isopropyl-1H-indazole-5-carboxylic acid methyl ester.

After the above-obtained 3-chloro-1-isopropyl-1H-indazole-5-carboxylic acid methyl ester was dissolved in tetrahydrofuran, lithium aluminum borohydride was added dropwise. After stirring at room temperature for 1 hour, water, 6N aqueous sodium hydroxide solution, and water were sequentially added. Celite was added dropwise, and the filtrate was distilled under reduced pressure. The residue was separated by column chromatography to obtain (3-chloro-1-isopropyl-1H-indazol-5-yl)-methanol.

(1-2) Synthesis of 1-chloro-6-hydroxy-3,4-dihydro-naphthalene-2-carbaldehyde

First, N,N-dimethylformamide (DMF) and phosphoryl chloride (phosphorous oxychloride, $POCl_3$) were added dropwise to a solution of 6-methoxy-3,4-dihydronaphthalen-1(2H)-one dissolved in toluene at 0° C., followed by stirring for 70° C. for 6 hours. The reaction mixture was poured into ice, and extraction with ethyl acetate was carried out. The organic layer was washed with brine, dried and concentrated, and then the obtained residue was purified by silica gel column chromatography (hexane:ethyl acetate=20:1 to 10:1) to obtain 1-chloro-6-methoxy-3,4-dihydro-2-naphthalene carbaldehyde.

Next, aluminum chloride ($AlCl_3$) was added to a solution of 1-chloro-6-methoxy-3,4-dihydro-2-naphthalene carbaldehyde dissolved in dichloromethane at 0° C., followed by stirring at 50° C. for 6 hours. The reaction mixture was poured into ice, and extraction with ethyl acetate was carried out. The organic layer was dried and concentrated, and then the obtained residue was purified by silica gel column chromatography (hexane:tetrahydrofuran=5:1 to 3:1) to obtain 1-chloro-6-hydroxy-3,4-dihydro-2-naphthalene carbaldehyde.

(1-3) Synthesis of 1-chloro-6-(3-chloro-1-isopropyl-1H-indazol-5-ylmethoxy)-3,4-dihydro-naphthalene-2-carbaldehyde (3-Chloro-1-isopropyl-1H-indazol-5-yl)-methanol and 1-chloro-6-hydroxy-3,4-dihydro-2-naphthalene carbaldehyde, which were obtained above, were dissolved in toluene, and then tributyl phosphine ($PBu_3$) and 1,1'-(azodicarbonyl) dipiperidine (ADD) were added dropwise. After stirring at room temperature for 18 hours, an excess amount of hexane was added. After filtration and distillation under reduced pressure, the residue was purified by column chromatography to obtain 1-chloro-6-(3-chloro-1-isopropyl-1H-indazol-5-ylmethoxy)-3,4-dihydro-naphthalene-2-carbaldehyde.

However, the above reactions may have the following problems in producing clinical APIs:

First, in the process of synthesizing 3-chloro-1-isopropyl-1H-indazole-5-carboxylic acid methyl ester, there may be a problem due to the production ratio of the N2 isomer. Lithium aluminum hydride (LAH) used for the synthesis of (3-chloro-1-isopropyl-1H-indazol-5-yl)-methanol has the following disadvantages: it has very limited stability for use in large scale synthesis and is easily decomposed by water.

In addition, during the Vilsmeier-Haack reaction to obtain 1-chloro-6-methoxy-3,4-dihydro-2-naphthalene carbaldehyde, the exothermic problem may arise as the reaction occurrs at a high temperature of 70° C. In addition, in the reaction to obtain 1-chloro-6-hydroxy-3,4-dihydro-2-naphthalene carbaldehyde, there may be a problem of reactor contamination due to the use of $AlCl_3$ or a stability problem due to the use of hazardous reagents. When $AlCl_3$ is used, there is a stability problem due to the occurrence of batch fail caused by reaction stop or side reaction progress, and the total yield is 70%, so there is a need to improve the yield.

In addition, 1,1'-(azodicarbonyl)dipiperidine (ADD), which is used for the coupling of (3-chloro-1-isopropyl-1H-indazol-5-yl)-methanol and 1-chloro-6-hydroxy-3,4-dihydro-naphthalene-2-carbaldehyde, is not preferable in terms of a low yield problem and cost.

In addition, there is a problem in that API reprocessing must be performed due to the impurity of the N2 isomer. The synthesis method is a linear process, and there was a problem in that the yield deteriorated whenever each process was performed. In addition, the synthesis method had a problem in that it was not easy to identify and solve the cause when a problem occurred in the intermediate process. For example, if impurities were not removed during recrystallization, the first step of the process must be started anew.

In particular, in scheme 1 above, in the step for preparing 1-[1-chloro-6-(3-chloro-1-isopropyl-1H-indazol-5-yl-methoxy)-3,4-dihydro-naphthalen-2-ylmethyl]piperidine-4-carboxylic acid from 1-chloro-6-(3-chloro-1-isopropyl-1H-indazol-5-ylmethoxy)-3,4-dihydro-naphthalene-2-carbaldehyde, the intermediate product, "1-[1-chloro-6-(3-chloro-1-isopropyl-1H-indazol-5-ylmethoxy)-3,4-dihydro-naphthalene-2-ylmethyl]-piperidine-4-carboxylic acid ethyl ester", has sticky oil properties, and thus, after completion of the reaction, the subsequent process was performed in a crude state without a separate purification step.

However, in order to improve the purity of the reaction and the purity of the final API in the subsequent API process, purification of the intermediate product 1-[1-chloro-6-(3-chloro-1-isopropyl-1H-indazol-5-ylmethoxy)-3,4-dihydro-naphthalen-2-ylmethyl]-piperidine-4-carboxylic acid ethyl ester was required. In particular, since it was not easy to remove impurities, such as the N2 isomer and the like, purification of intermediate products is absolutely necessary.

Accordingly, there remains a need to develop a new synthesis method for converting conventional linear processes into effective convergent synthesis methods while improving the purity and yield of a product.

BRIEF SUMMARY

Technical Problem

Thus, an aspect of the present invention provides a suitable method for producing a compound of Formula 7 or a salt thereof, which can be used as an excellent sphingosine-1-phosphate receptor agonist, with high yield and high purity:

[Formula 7]

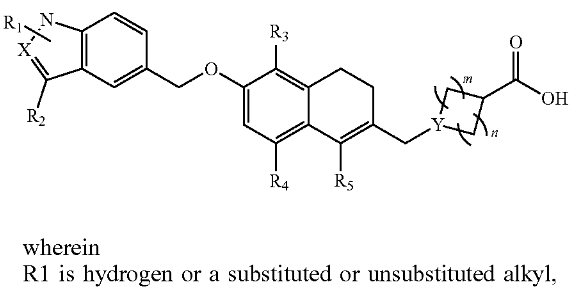

wherein

R1 is hydrogen or a substituted or unsubstituted alkyl,

R2 is hydrogen, a substituted or unsubstituted alkyl, a halogen, CN, $CF_3$, or $COCF_3$, R3 and R4 are each hydrogen, a substituted or unsubstituted alkyl, or a halogen, R5 is hydrogen, a substituted or unsubstituted alkyl, or a halogen, X is C or N, Y is N, O, or S, and m and n are each 0, 1, 2, or 3, and m+n>0.

Technical Solution

According to an aspect of the present invention, there is provided a method for preparing a compound of Formula 7 below or a salt thereof, comprising:

1) a step for preparing a compound of Formula 4 by coupling a compound of Formula 2 with a compound of Formula 3 in the presence of dimethylacetamide (DMA) solvent;
2) a step for reacting a compound of Formula 4 and a compound of Formula 5 under a reducing condition to prepare a compound of Formula 6 or a salt thereof; and
3) a step for converting an ester group of the compound of Formula 6 or the salt thereof to a carboxylic acid group to prepare a compound of Formula 7 or a salt thereof:

[Formula 2]

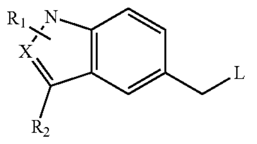

[Formula 3]

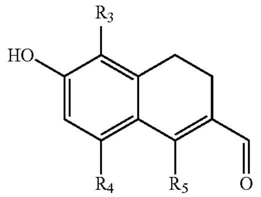

[Formula 4]

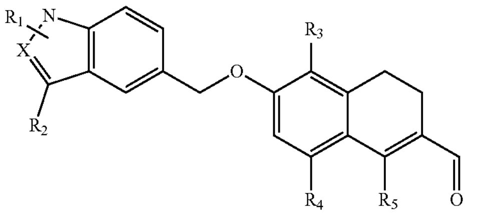

[Formula 5]

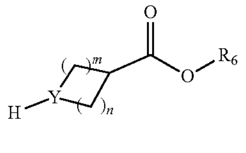

[Formula 6]

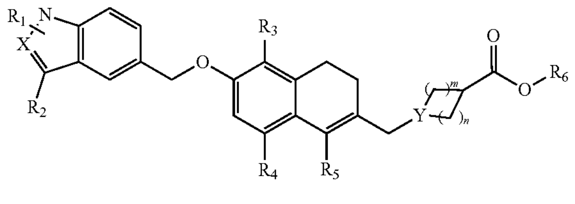

-continued

[Formula 7]

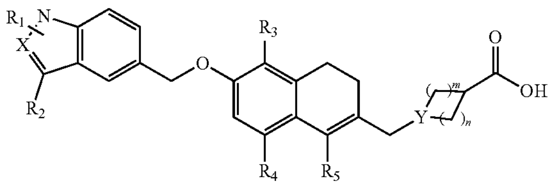

wherein

R1 is hydrogen or a substituted or unsubstituted alkyl,

R2 is hydrogen, a substituted or unsubstituted alkyl, a halogen, CN, $CF_3$, or $COCF_3$, R3 and R4 are each hydrogen, a substituted or unsubstituted alkyl, or a halogen, R5 is hydrogen, a substituted or unsubstituted alkyl, or a halogen, R6 is a substituted or unsubstituted alkyl, X is C or N, Y is N, O, or S, L is a leaving group, and m and n are each 0, 1, 2, or 3, and m+n>0.

When the 'alkyl' is substituted, there may be one or more substituents, and the substituents may be each independently selected from the group consisting of a halogen, cyano, hydroxy, alkyloxy, oxo, an unsubstituted sulfonyl, and a sulfonyl substituted with an alkyl.

According to one embodiment of the present invention, R1 of the above formulae may be hydrogen or a $C_1$-$C_6$ substituted or unsubstituted alkyl, and R2 may be hydrogen, a $C_1$-$C_6$ substituted or unsubstituted alkyl, a halogen, CN, $CF_3$, or $COCF_3$. R3 and R4 may be each hydrogen or a $C_1$-$C_6$ substituted or unsubstituted alkyl. R5 may be F, Cl, Br, or I. In addition, R6 may be a $C_1$-$C_4$ substituted or unsubstituted alkyl.

According to another embodiment of the present invention, R1 may be a $C_1$-$C_4$ substituted or unsubstituted alkyl, and R2 may be a halogen (F, Cl, Br, or I). R3 and R4 may be each hydrogen. R5 may be Cl. In addition, R6 may be an ethyl group.

According to one embodiment of the present invention, the leaving group (L) is a reactive group that provides a substitution position to the compound of Formula 2 when the compound of Formula 2 is subjected to a substitution reaction with an alcohol-based compound, such as Formula 3, and may be, without limitation, selected from among chlorine (Cl), bromine (Br), iodine (I), methanesulfonate (Oms), p-toluenesulfonate (OTs), and trifluoromethanesulfonate (OTf).

According to another embodiment of the present invention, L may be Br.

According to one embodiment of the present invention, Y may be N or O, and it may be m>0, n>0, and m+n=3 or 4.

According to another embodiment of the present invention, Y may be N, and m and n may be each 2.

In the present invention, in referring to 'a compound or a salt thereof,' the term 'salt thereof' refers to a pharmaceutically acceptable salt of the compound.

The pharmaceutically acceptable salts include acid-addition salts which are formed from inorganic acids, such as hydrochloric acid, sulfuric acid, nitric acid, phosphoric acid, hydrobromic acid, and hydroiodic acid; organic acids, such as tartaric acid, formic acid, citric acid, acetic acid, trichloroacetic acid, trifluoroacetic acid, gluconic acid, benzoic acid, lactic acid, fumaric acid, and maleic acid; or sulfonic acids, such as methanesulfonic acid, benzenesulfonic acid, p-toluenesulfonic acid, or naphthalene-sulfonic acid, which form non-toxic acid-addition salts containing pharmaceutically acceptable anions. Particularly, preferable acid-addition salts are formed from sulfuric acid, methanesulfonic acid, or a hydrohalic acid.

In one embodiment of the present invention, the salt of the compound of Formula 6 and the salt of the compound of Formula 7 may be the hydrochloride salt of the compound of Formula 6 and the hydrochloride salt of the compound of Formula 7, respectively.

DETAILED DESCRIPTION

Hereinafter, the present invention will be described in more detail.

In the present invention, in step 1), the compound of Formula 4 is prepared by coupling the compound of Formula 2 with the compound of Formula 3 in the presence of dimethylacetamide (DMA) solvent.

In one embodiment, according to the present invention, coupling the compound of Formula 2 with the compound of Formula 3 can be easily performed using $K_2CO_3$ in DMA solvent.

In the coupling, when the reaction solvent is unstable and thus decomposed, the decomposition product may react with the reactant of the synthesis reaction to generate impurities, thereby reducing the purity of the reaction product. In this regard, since the maximum temperature of synthesis reaction and the degree of adiabatic temperature rise for the synthesis reaction in which dimethylformamide is used as the reaction solvent are higher than those for the synthesis reaction in which dimethylacetamide is used as the reaction solvent, it may be preferable to use dimethylacetamide as the reaction solvent for the synthesis reaction.

In another embodiment, according to the present invention, the compound of Formula 4 with high purity can be obtained by performing a step for crystallizing the compound of Formula 4 after coupling the compound of Formula 2 with the compound of Formula 3.

In one embodiment, according to the present invention, there may be a problem in that crystallization does not proceed depending on a solvent used for crystallization of the compound of Formula 4, and it may be preferable that the solvent for crystallization of the compound of Formula 4 includes an alcohol-based solvent. For example, when water or methyl tert-butyl ether (MTBE) is used alone during the crystallization of the compound of Formula 4, crystallization may not proceed.

In one embodiment, according to the present invention, the solvent for the crystallization may be a mixed solvent of an alcohol-based solvent, an ester-based solvent, a non-polar solvent, and water. Using a mixed solvent of an alcohol-based solvent, an ester-based solvent, a non-polar solvent, and water as the crystallization solvent can lead to the crystallization of the compound of Formula 4 and allow for the obtainment of the compound of Formula 4 with high yield.

The 'alcohol-based solvent' for the crystallization of the compound of Formula 4 may be, without limitation, one or more solvents selected from among methanol, ethanol, isopropyl alcohol, and butanol, for example.

The 'ester-based solvent' for the crystallization of the compound of Formula 4 may be, without limitation, one or more solvents selected from among methyl acetate, ethyl acetate, and isopropyl acetate, for example.

The 'non-polar solvent' for the crystallization of the compound of Formula 4 may be, without limitation, one or more solvents selected from among pentane, hexane, and heptane, for example.

In another embodiment, according to the present invention, the solvent for crystallization may be a mixed solvent of ethanol, isopropyl acetate, heptane, and water.

In the present invention, in step 2), the compound of Formula 6 or a salt thereof is prepared by reacting the compound of Formula 4 and the compound of Formula 5 under a reducing condition.

When the compound of Formula 4 and the compound of Formula 5 are mixed under a reducing condition, a bond with a hetero atom represented by Y of the compound of Formula 5 is formed at the carbon position of the carbonyl (C═O) functional group of Formula 4, and the carbonyl functional group is reduced so that the compound of Formula 6 can be prepared, but the mechanism of the present invention is not limited thereto.

In one embodiment of the present invention, the compound of Formula 6 is prepared by reacting the compound of Formula 4 and the compound of Formula 5 in the presence of a reducing agent.

The reducing agent may be, without limitation, at least one selected from among sodium triacetoxyborohydride ($NaBH(OAc)_3$), sodium borohydride ($NaBH_4$), and sodium cyanoborohydride ($NaBH_3CN$), for example.

In another embodiment of the present invention, the compound of Formula 4 and the reducing agent may be used in an equivalent ratio of 1:5 to 5:1 in terms of reaction efficiency. For example, the compound of Formula 4 and the reducing agent may be used in an equivalent ratio of 1:4 to 4:1, 1:3 to 3:1, or 1:2 to 2:1.

In one embodiment of the present invention, a pharmaceutically acceptable salt of the compound of Formula 6 may be obtained following the condition for obtaining the compound of Formula 6 in step 2).

In another embodiment of the present invention, hydrochloride of the compound of Formula 6 may be prepared through crystallization after completing the reaction between the compound of Formula 4 and the compound of Formula 5 in step 2).

In one embodiment of the present invention, the crude compound of Formula 6 prepared by the reaction between the compound of Formula 4 and the compound of Formula 5 in step 2) may exhibit sticky oil properties and thus can be further subjected to a step for crystallizing after completing the reaction, thereby obtaining the compound of Formula 6 or a salt thereof.

In one embodiment of the present invention, the crude compound of Formula 6 may be crystallized under an acidic condition.

The acidic condition may be, for example, a condition of pH 3.0 or less. Specifically, crystallization may be performed by adding an acid compound so that the pH of a solution containing the compound of Formula 6 is 1.0 to 3.0.

For the acid compound used to make the acidic condition, a known acid compound may be used within a range in which the structure and physical properties of the compound of Formula 6 are not damaged, and the type of the acid compound is not limited.

According to one embodiment of the present invention, crystallization may be performed by adding hydrochloric acid (HCl) to the crude reaction product containing the compound of Formula 6.

According to another embodiment of the present invention, the hydrochloric acid may be used in a concentration of 1 N to 8 N. Preferably, the hydrochloric acid may be used in a concentration of 3 N to 6 N. If the hydrochloric acid concentration is too high, the amount of water used during crystallization is insufficient, so the removal rate of the B complex is poor, and thus a problem in that the filtration does not proceed may occur.

According to one embodiment of the present invention, the crystallization may be performed at a temperature of 25° C. or less, for example, at a temperature of 0° C. to 25° C., but the crystallization temperature is not limited thereto.

According to another embodiment of the present invention, the crystallization may be performed at a temperature of 0° C. to 20° C., for example, a temperature of 10° C.

According to one embodiment of the present invention, the crystallization may be performed according to an anti-solvent method.

The solvent for the crystallization according to the anti-solvent method may be one or more solvents selected from among water; polar organic solvents, such as methyl tertiary butyl ether (MTBE), ethyl acetate (EA), dichloromethane (DCM), and the like; and non-polar organic solvents, such as n-hexane and the like.

According to another embodiment of the present invention, the solvent for the crystallization may be an ether-based single solvent.

In the present invention, the 'single solvent' refers to the addition of only one solvent for the crystallization of the compound of Formula 6. It is obvious to a person skilled in the art that the case, in which crystallization is performed without distilling the reaction solvent after the reaction for preparing the compound of Formula 6 so that the reaction solvent remains in the reactor and then one solvent for the crystallization is added, is not excluded from the 'single solvent.'

In addition, the inclusion of a heterogeneous solvent in a trace amount corresponding to a level at which the crystallization yield is not substantially affected when the one solvent is added is also not excluded from the single solvent. For example, the inclusion of a heterogeneous solvent in a content of 5 vol % or less, 4 vol % or less, 3 vol % or less, 2 vol % or less, 1 vol % or less, 0.5 vol % or less, or 0 vol % (i.e., no inclusion) based on the total volume of the solvent added for crystallization can be said as the use of the single solvent.

Examples of the ether-based solvent include, but are not limited to, dialkyl ether-based solvents, such as diethyl ether, dipropyl ether, dibutyl ether, diisoamyl ether, ethyl methyl ether, methyl propyl ether, methyl butyl ether, and ethyl propyl ether: arylalkyl ether-based solvents, such as diphenyl ether and anisole; or cyclic ether-based solvents, such as tetrahydrofuran and tetrahydropyran; and so on.

According to one embodiment of the present invention, the ether-based single solvent may be methyl tert-butyl ether (MTBE).

According to one embodiment of the present invention, the solvent for the crystallization may be added in an amount required for crystallization so that crystallization is performed, and the amount of solvent used is not particularly limited.

According to another embodiment of the present invention, the solvent for the crystallization may be used in an amount of 4 to 10 times the amount of the solution to be crystallized.

According to another embodiment, according to the present invention, crystallization may be performed by adding 4- to 8-fold, specifically 6-fold, of MTBE to the crude reaction product containing the compound of Formula 6.

In the present invention, in step 3), the compound of Formula 7 or a salt thereof is prepared by converting the ester group of the compound of Formula 6 or the salt thereof obtained above to a carboxylic acid group.

For the compound of Formula 6 in step 3), the crude reaction product obtained by completing the reaction in step 2) and then not performing purification and crystallization may be used as it is, or the reaction product obtained by completing the reaction in step 2) and then performing purification and/or crystallization may be used. But, the compound of Formula 6 in step 3) is not limited thereto.

In one embodiment of the present invention, a pharmaceutically acceptable salt of the compound of Formula 6 obtained through crystallization in step 2), such as hydrochloride of the compound of Formula 6, may be used as a reactant in step 2).

In one embodiment of the present invention, the ester group may be converted to a carboxylic acid group by reacting the compound of Formula 6 or the salt thereof with water, a polar solvent, or a mixed solvent thereof in the presence of a base.

Examples of a polar solvent that can be used for the conversion to a carboxylic acid group include, without limitation, an alcohol-based solvent, such as methanol, ethanol, n-propanol, isopropanol, n-butanol, iso-butanol, sec-butanol, and tert-butanol; and a polar non-alcohol-based solvent, such as chloromethane and dichloromethane.

In one embodiment of the present invention, when methanol is used for converting to a carboxyl group, a methyl ester-type impurity may be generated by methanol remaining in a subsequent API process. Thus, the compound of Formula 7 or a salt thereof may be prepared using ethanol.

In another embodiment of the present invention, ethanol, water, dichloromethane, or a mixed solvent thereof may be used as the reaction solvent for conversion to a carboxyl group.

In one embodiment of the present invention, a base that can be used for converting to a carboxyl group may be selected from among sodium hydroxide, potassium hydroxide, lithium hydroxide, and barium hydroxide.

In another embodiment of the present invention, the base may be used in an aqueous solution state or a solid state. Using a base in a solid state may lead to an excellent effect in terms of the ease of storage and use of raw material.

In another embodiment of the present invention, the compound of Formula 6 or the salt thereof and ethanol may be mixed in the presence of NaOH, and the compound of Formula 7 or a salt thereof may be prepared at a temperature of 40 to 60° C.

In one embodiment of the present invention, the reaction may be carried out using 3 to 5 equivalents of the base and 5 to 7 equivalents of the solvent in terms of the purity of the product.

In the present invention, the method may further include 4) a step for recrystallizing the compound of Formula 7 or the salt thereof obtained in step 3) under an acidic condition.

The recrystallization in step 4) may be to make the content of dichloromethane (DCM) solvent in the obtained product containing the compound of Formula 7 or the salt thereof, such as the fraction containing the compound of Formula 7 or the salt thereof, which has been recrystallized, 600 ppm or less. However, the purpose of the present invention is not limited thereto.

In one embodiment of the present invention, the content of DCM solvent in the fraction obtained after the recrystallization can be measured, for example, through HPLC.

In the present invention, the crystallization of the compound of Formula 7 or the salt thereof is performed under an acidic condition. The acidic condition may be, for example, a condition of pH 3 or less. Specifically, crystallization may be performed by adding an acid compound so that the pH of a solution containing the compound of Formula 7 is 1 to 3.

For the acid compound used to make the acidic condition, a known acid compound may be used within a range in which the structure and physical properties of the compound of Formula 7 or a salt thereof are not damaged, and the type of the acid compound is not limited.

According to one embodiment of the present invention, crystallization may be performed by adding hydrochloric acid (HCl) to the reaction product containing the compound of Formula 7 or a salt thereof.

Examples of the solvent for the recrystallization may include, without limitation, one or more solvents selected from among water: ester solvents, such as methyl acetate (MeOAc), ethyl acetate (EtOAc), and isopropyl acetate (IPOAc), alcohol solvents, such as methanol (MeOH), ethanol (EtOH), and isopropyl alcohol (IPA), and polar organic solvents, such as methyl tert-butyl ether (MTBE), dichloromethane (DCM), and tetrahydrofuran (THF); and non-polar organic solvents, such as n-hexane and xylene.

In one embodiment of the present invention, the recrystallization step may be performed using a mixed solvent of water, ethyl acetate, and ethanol.

In another embodiment of the present invention, the recrystallization step may be performed using a mixed solvent of water, isopropyl acetate, and ethanol.

In another embodiment of the present invention, the recrystallization step may be performed using a mixed solvent of 4- to 6-fold of water, 1- to 3-fold of isopropyl acetate, and 1- to 3-fold of ethanol compared to the compound to be recrystallized.

In another embodiment of the present invention, the recrystallization step may be performed using a mixed solvent of 5-fold of water, 2-fold of isopropyl acetate, and 2-fold of ethanol compared to the compound to be recrystallized.

In another embodiment of the present invention, the recrystallization step may be performed by including the same kind of solvent as the solvent remaining in step 3).

In one embodiment of the present invention, the recrystallization step may include adding an acid compound at a temperature of 0-25° C.

In another embodiment of the present invention, the recrystallization step may include adding an acid compound at a temperature of 20-25° C.

In one embodiment of the present invention, the recrystallization step may be performed without or with stirring.

In another embodiment of the present invention, the recrystallization step may be performed, for example, while stirring at a speed of 100 to 500 rpm after an acid compound addition.

In another embodiment of the present invention, the recrystallization step may be performed while stirring at a speed of 400 to 500 rpm after an acid compound addition.

In one embodiment of the present invention, the recrystallization step may be performed, for example, while adding an acid compound dropwise for 100 minutes.

In another embodiment of the present invention, the recrystallization step may be performed while adding an acid compound dropwise for 10 to 60 minutes.

The recrystallization step may be performed one or more times to improve the yield and purity of the product excellently.

When the recrystallization step is performed under the same conditions as described above, the product with high yield and high purity can be obtained by only one recrystallization of the compound of Formula 7 or the salt thereof.

According to another aspect of the present invention, the compound of Formula 3 may be prepared from a compound of Formula 8.

[Formula 3]

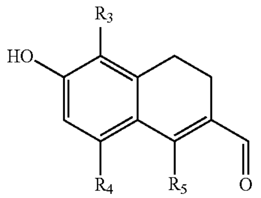

[Formula 8]

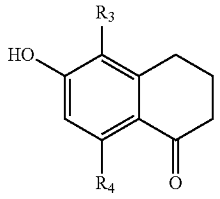

Specifically, the compound of Formula 3 may be obtained by introducing an aldehyde into the compound of Formula 8.

In one embodiment, according to the present invention, the reaction of introducing an aldehyde into the compound of Formula 8 may be performed using reagents for the Vilsmeier-Haack reaction.

In another embodiment, according to the present invention, the reaction of introducing an aldehyde into the compound of Formula 8 may be reacting the compound of Formula 8 with phosphoryl chloride ($POCl_3$) and dimethylformamide (DMF) to prepare the compound of Formula 3.

In one embodiment, according to the present invention, the reaction of introducing an aldehyde into the compound of Formula 8 may be performed at a temperature of 30° C. or less, thereby stabilizing the exothermic problem caused by the Vilsmeier-Haack reaction.

In another embodiment, according to the present invention, the reaction of introducing an aldehyde into the compound of Formula 8 may be performed at a temperature of 0° C. to 25° C.

In another embodiment of the present invention, the reaction of introducing an aldehyde to the compound of Formula 8 may consist of:

1) a step for preparing a compound of Formula 9 by blocking the alcohol group of the compound of Formula 8, 2) a step for preparing a compound of Formula 10 by introducing an aldehyde into the compound of Formula 9, and 8) a step for preparing the compound of Formula 3 by restoring an alcohol group from the compound of Formula 10,

[Formula 8]

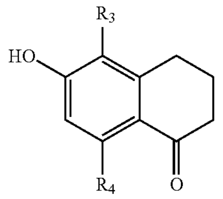

[Formula 9]

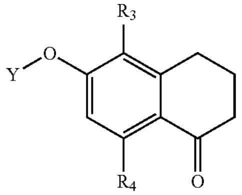

[Formula 10]

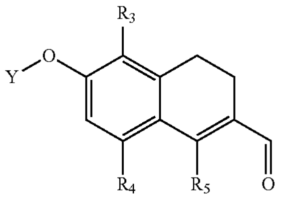

wherein Y is an alcohol-protecting group.

In the present invention, an aldehyde is introduced without blocking the alcohol group of the compound of Formula 8, and the compound of Formula 3 may be prepared by simplifying the process. However, in terms of the yield of the compound of Formula 3, the aldehyde introduction reaction may be performed after blocking the alcohol group of the compound of Formula 8 with an alcohol-protecting group.

Blocking the alcohol group in the compound of Formula 8 may be performed according to a known alcohol blocking method, and the method is not particularly limited.

Accordingly, the alcohol protecting group (Y) introduced into the compound of Formula 8 is not particularly limited as long as it is a known alcohol protecting group. Examples include, without limitation, an acetyl group (—Ac), a trimethylsilyl group (-TMS), a tert-butyldimethylsilyl group (-TBDMS), and the like.

The step for preparing the compound of Formula 10 by introducing the aldehyde into the compound of Formula 9 in which the alcohol has been blocked may be performed according to the same method as the step for introducing the aldehyde into the compound of Formula 5 in which the alcohol group is not blocked.

Next, after preparing the compound of Formula 10 by introducing an aldehyde into the compound of Formula 9, the alcohol group may be restored using a suitable alcohol de-blocking agent depending on the alcohol-protecting group to prepare the compound of Formula 3.

According to one embodiment of the present invention, for the alcohol de-blocking agent, a known alkaline material may be used. Examples of the known alkaline material include, without limitation, $K_2CO_3$, $NaHCO_3$, NaOH, and the like.

In the present invention, the reaction solvent may be appropriately selected depending on the type of de-blocking agent used in the alcohol restoration reaction.

According to one embodiment of the present invention, when an alkaline material, such as $K_2CO_3$, $NaHCO_3$, and NaOH, is used as the alcohol de-blocking agent, the reaction solvent may be an alcohol-based solvent, for example, methanol, ethanol, or a mixed solvent thereof.

According to another embodiment of the present invention, when at least one of $K_2CO_3$ and $NaHCO_3$ is used as the alcohol de-blocking agent, and the reaction solvent is methanol, an excellent effect can be exhibited in terms of the reaction time and the yield of the alcohol restoration reaction.

According to one embodiment of the present invention, the compound of Formula 3 may be prepared by blocking the alcohol group in the compound of Formula 8 using acetyl chloride (AcCl), introducing an aldehyde group using $POCl_3$ and DMF, and then using $K_2CO_3$ in an alcohol-based solvent.

According to another embodiment of the present invention, the compound of Formula 3 may be prepared by blocking the alcohol group in the compound of Formula 8 using acetyl chloride (AcCl), introducing an aldehyde group using $POCl_3$ and DMF, and then using $K_2CO_3$ in methanol solvent.

In the present invention, the compound of Formula 3 with high purity may be obtained through crystallization of the compound of Formula 3 prepared as described above.

According to one embodiment of the present invention, the compound of Formula 3 is prepared through a series of steps without a purification process between each step, and thus the purity can be improved through crystallization.

In the present invention, the crystallization of the compound of Formula 3 may be performed under an acidic condition. The acidic condition may be, for example, a condition of pH 4.0 or less. Specifically, crystallization may be performed by adding an acid compound so that the pH of a solution containing the compound of Formula 3 is 3.0 to 4.0.

For the acid compound used to make the acidic condition, a known acid compound may be used within a range in which the structure and physical properties of the compound of Formula 3 are not damaged, and the type of the acid compound is not limited.

According to one embodiment of the present invention, crystallization may be performed by adding hydrochloric acid (HCl) to the reaction product containing the compound of Formula 3.

According to another embodiment of the present invention, crystallization may be performed by adding water ($H_2O$) and hydrochloric acid (HCl) simultaneously or sequentially to the reaction product containing the compound of Formula 3.

According to another embodiment of the present invention, crystallization may be performed by adding water and then adding hydrochloric acid (HCl) to the reaction product containing the compound of Formula 3.

According to one embodiment of the present invention, crystallization of the compound of Formula 3 may be performed after terminating the reaction for restoring the alcohol group and then distilling off the reaction solvent, such as methanol.

According to another embodiment of the present invention, crystallization of the compound of Formula 3 may be performed after terminating the reaction for restoring the alcohol group and then no distilling off the reaction solvent, such as methanol. Performing the crystallization without the reaction solvent in the step for restoring the alcohol group can reduce the loss of the compound of Formula 3, thereby improving the yield.

According to one embodiment of the present invention, the crystallization of the compound of Formula 3 may be performed at a reaction temperature of 10° C. or less.

According to another embodiment of the present invention, during crystallization of the compound of Formula 3, the reaction temperature may be 10° C. or less, and adding dropwise hydrochloric acid may be performed for less than 2 hours, for example, 1 hour, 30 minutes, 20 minutes, or 10 minutes or less.

In another embodiment of the present invention, the compound of Formula 8 may be prepared by performing the dealkylation of a compound of Formula 11:

[Formula 11]

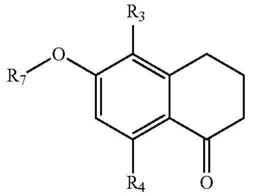

wherein R3 and R4 are as defined above, and R7 is a substituted or unsubstituted alkyl.

In one embodiment of the present invention, R7 may be a $C_1$-$C_4$ unsubstituted alkyl.

In another embodiment of the present invention, R7 may be a methyl group.

The compound of Formula 3 may be prepared by introducing an aldehyde into the compound of Formula 11 according to the same method as for introducing an aldehyde into the compound of Formula 8 or Formula 9. However, in one embodiment of the present invention, by performing the dealkylation of the compound of Formula 11 to prepare the compound of Formula 8 and introducing an aldehyde to the compound of Formula 8 or 9 to prepare the compound of Formula 3, the problem of decomposition of the compound of Formula 11 can be improved and the intermediate compound can be prepared with high yield even in mass production.

The dealkylation of the compound of Formula 11 may be performed according to a known method by which the alkyl group of R7 is substituted with an alcohol group to prepare the compound of Formula 8, and the method and the type of reagent used are not particularly limited.

In one embodiment of the present invention, the dealkylation of the compound of formula 11 may be performed using, for example, hydrogen bromide (HBr), aluminum chloride ($AlCl_3$), and iron (III) chloride ($FeCl_3$). But the present invention is not limited thereto.

The compound prepared according to the present invention or the salt thereof may be used as a sphingosine-1-phosphate receptor agonist, but the compound prepared according to the present invention may be used for other purposes other than the use as a sphingosine-1-phosphate receptor agonist. The use of the present invention is not limited to that as a sphingosine-1-phosphate receptor agonist.

Advantageous Effects

Using the preparation method of the present invention can lead to mass production of the compound of Formula 7 with high yield and high purity.

Figure 1:
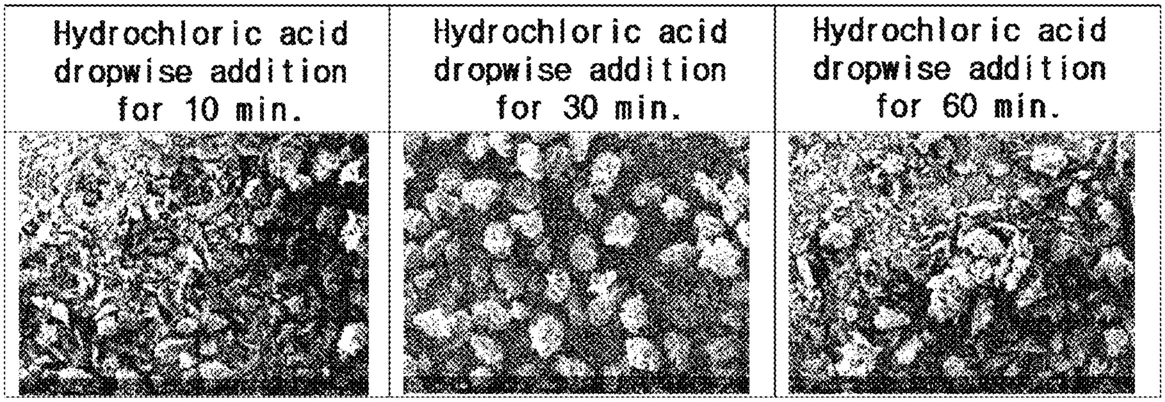
FIG. 1 is the SEM photograph of crystals generated when the dropwise addition time of hydrochloric acid is changed according to Experimental Example 2.

Hereinafter, to help the understanding of the present invention, the present invention will be described in more detail by examples. However, examples according to the present invention may be modified into various other types, and the scope of the present invention should not be construed as being limited to the following examples. The examples of the present invention are provided for completely explaining the present invention to a person having an average knowledge in the art to which the present invention belongs.

EXAMPLE 1. Synthesis of (1-chloro-6-(3-chloro-1-isopropyl-1H-indazol-5-ylmethoxy)-3,4-dihydro-naphthalene-2-carbaldehyde)

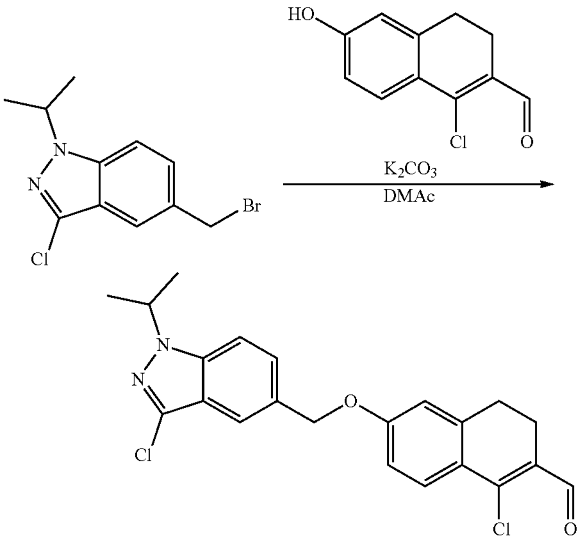

5-Bromomethyl-3-chloro-1-isopropyl-1H-indazole (16.54 g, 57.5 mol), 1-chloro-6-hydroxy-3,4-dihydronaphthalene-2-carbaldehyde (10 g, 47.9 mmol), $K_2CO_3$ (3.62 kg, 26.2 mol), and dimethylacetamide (DMA, 50 mL, 5-fold) were placed into the reactor and reacted at an internal temperature of 25° C. for 16 hours.

The reaction IPC was carried out by HPLC, and the reaction was completed (1-chloro-6-hydroxy-3,4-dihydronaphthalene-2-carbaldehyde: N/D). DCM (100 ml, 10-fold) and water (100 ml, 10-fold) were added and stirred for 30 minutes, and the first layer separation proceeded. Water (50 ml, 5-fold) was added to the reaction and stirred for 10 minutes, and the second layer separation proceeded. Finally, water (50 ml, 5-fold) was added and stirred for 10 minutes, and layer separation proceeded.

The reaction mixture was distilled under reduced pressure. The mixture of EtOH (10 ml, 1-fold), IPOAc (10 ml, 1-fold), and heptane (60 ml, 6-fold) was added to the reaction mixture containing the crude title compound obtained after DCM distillation. Then, the internal temperature was set to 60° C., stirring for 1 hour was performed, and then cooling to room temperature was carried out. After the internal temperature reached 20° C., the crystals were aged for 1 hour, and then filtration was performed. The filtered solid was washed twice with water (60 ml, 6-fold) and dried with nitrogen to synthesize the title compound (20.3 g, net yield 85%).

1H NMR (500 MHZ, CDCl3): 1.57 (d, 6H), 2.62 (m, 2H), 2.80 (t, 2H), 4.79 (m, 1H), 5.19 (s, 2H), 6.82-6.93 (m, 2H), 7.42-7.50 (m, 2H), 7.71(s, 1H), 7.80 (d, 1H), 10.33 (s, 1H).

EXAMPLE 2. Synthesis of 1-[1-chloro-6-(3-chloro-1-isopropyl-1H-indazol-5-ylmethoxy)-3,4-dihydronaphthalen-2-ylmethyl]-piperidine-4-carboxylic acid ethyl ester hydrochloride

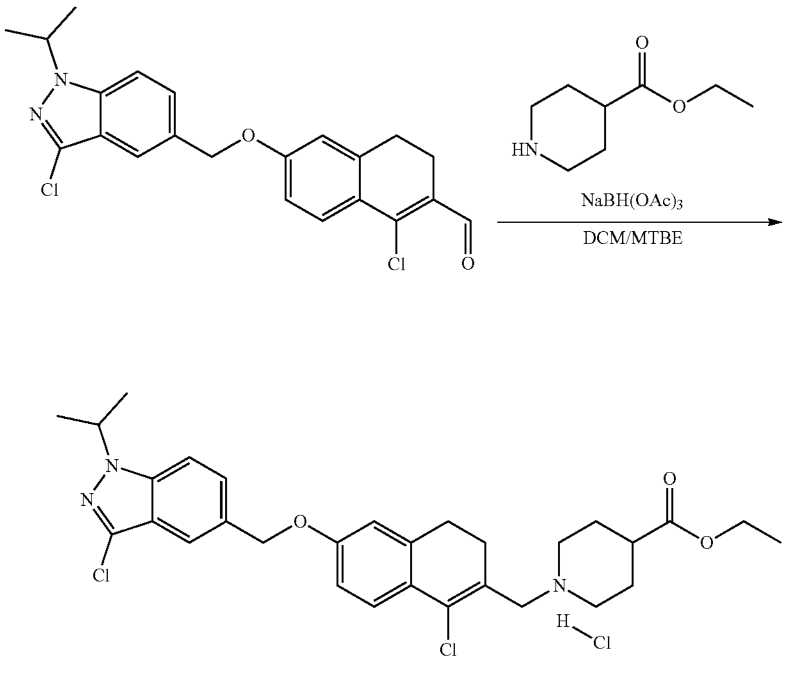

Into the reactor, 1-chloro-6-(3-chloro-1-isopropyl-1H-indazol-5-ylmethoxy)-3,4-dihydro-naphthalene-2-carbaldehyde (339.44 g, 0.82 mol), triethylamine (TEA, 83 g, 0.82 mol)), DCM (1.36 L, 4-fold), MTBE (678 ml, 2-fold), and ethyl isonipecotate (160.61 g, 1.02 mol) were placed. After stirring for 30 minutes, $NaBH(OAc)_3$ (268.5 g, 1.27 mol) was added and the reaction was allowed to proceed for 2 hours.

The reaction IPC was performed HPLC, and the reaction was completed (1-chloro-6-(3-chloro-1-isopropyl-1H-indazol-5-ylmethoxy)-3,4-dihydro-naphthalene-2-carbaldehyde: N/D). After cooling to the internal temperature of 10° C., 3 N HCl (1.09 L, 4 equiv) was added dropwise, MTBE (2.04 L, 6-fold) was added, the crytals were aged for 1 hour, and then filtration was performed. The filtered solid was washed once with water (1.70 L, 5-fold), once with water (1.02 L, 3-fold), once with MTBE (1.70 L, 5-fold), and once with MTBE (1.02 L, 3-fold), dried with nitrogen to synthesize the title compound (462.8 g, net yield 96%).

1H NMR (500 MHZ, CDCl3): 1.25 (t, 3H), 1.61 (d, 6H), 1.78 (m, 2H), 1.91 (m, 2H), 2.12 (t, 2H), 2.29-2.35 (m, 1H), 2.52 (t, 2H), 2.82 (t, 2H), 2.89-2.92 (m, 2H), 3.3 (s, 2H), 4.16 (q, 2H), 4.8-4.87 (m, 1H), 5.2 (s, 2H), 6.83-6.9 (m, 2H), 7.46-7.60 (m, 3H), 7.76(s, 1H).

EXAMPLE 3. Synthesis of 1-[1-chloro-6-(3-chloro-1-isopropyl-1H-indazol-5-ylmethoxy)-3,4-dihydro-naphthalen-2-ylmethyl]-piperidine-4-carboxylic acid hydrochloride

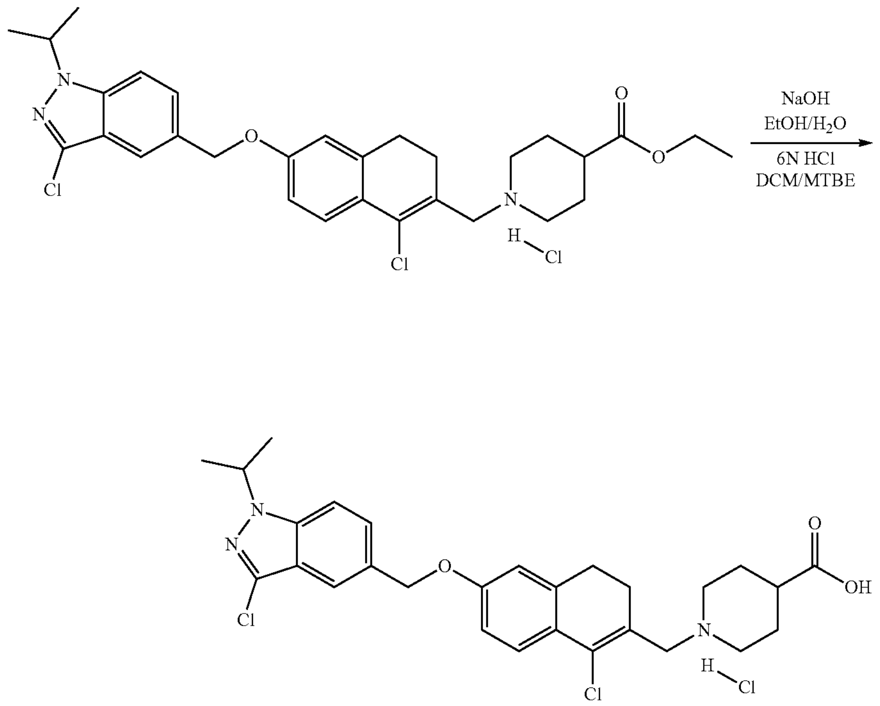

1-[1-Chloro-6-(3-chloro-1-isopropyl-1H-indazol-5-yl-methoxy)-3,4-dihydro-naphthalen-2-ylmethyl]-piperidine-4-carboxylic acid ethyl ester (462.8 g, 0.78 mol), EtOH (1.40 L, 3-fold), water (0.92 L, 2-fold), DCM (0.09 L, 0.2-fold), and NaOH (116 g, 2.90 mol) were placed into the reactor. The reaction was carried out at the internal temperature of 60° C. for 2 hours and 20 minutes. As a result of the reaction IPC by HPLC, the reaction was completed (1-[1-chloro-6-(3-chloro-1-isopropyl-1H-indazole-5-yl-methoxy)-3,4-dihydro-naphthalen-2-ylmethyl]-piperidine-4-carboxylic acid ethyl ester: N/D). So, cooling to the internal temperature of 20° C. was performed.

DCM (0.60 L, 1.3-fold) was added to the reaction mixture, 6 N HCl (0.50 L, 3.37 mol) was slowly added dropwise for 1 hour and 45 minutes to acidify the solution to pH 0.98, and then MTBE (4.60 L, 10-fold) was added to perform crystallization. Cooling to the internal temperature of 5° C., aging for 45 minutes, filtration, washing twice with water (2.06 L, 5-fold), washing once with MTBE (1.24 L, 3-fold), and drying with nitrogen were performed to synthesize the title compound (435.6 g, net yield 99%).

1H NMR (400 MHz, DMSO): 1.56 (d, 6H), 2.2 (d, 2H), 2.59 (t, 2H), 2.72 (bs, 1H), 2.93 (t, 2H), 3.25 (bs, 2H), 3.59 (bs, 2H), 4.18 (s, 2H), 4.95 (m, 1H), 5.26 (s, 2H), 6.95-6.99 (m, 2H), 7.55-7.66 (m, 3H), 7.72(s, 1H).

EXAMPLE 4

Crystallization of 1-[1-chloro-6-(3-chloro-1-isopropyl-1H-indazol-5-ylmethoxy)-3,4-dihydro-naphthalen-2-ylmethyl]-piperidine-4-carboxylic acid hydrochloride

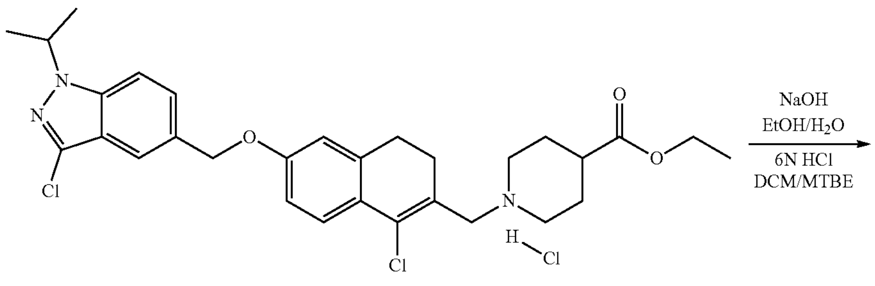

-continued

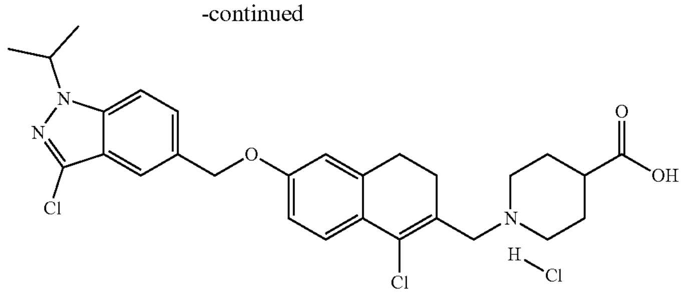

Example 3 (5.10 kg, 9.0 mol), EtOH (0.77 L, 2-fold), water (1.92 L, 5-fold), IPOAc (0.77 L, 2-fold), and NaOH (54.4 g, 1.36 mol) were placed into the reactor. Heating at the internal temperature of 45° C. was performed for 1 hour, and then cooling to the internal temperature of 20° C. was performed. 6 N HCl (290 ml) was added dropwise to the reaction mixture for 1 hour and 50 minutes to acidify the solution to pH 1.05, aging for 50 minutes was performed, and then filtration was performed. The filtered solid was washed twice with water (1.92 L, 5-fold) and once with MTBE (1.15 L, 3-fold), and then dried with nitrogen to synthesize the title compound (368 g, GMP step yield 79%).

1H NMR (400 MHZ, $CD_3OD$): 1.56 (d, 6H), 2.2 (d, 2H), 2.59 (t, 2H), 2.72 (bs, 1H), 2.93 (t, 2H), 3.25 (bs, 2H), 3.59 (bs, 2H), 4.18 (s, 2H), 4.95 (m, 1H), 5.26 (s, 2H), 6.95-6.99 (m, 2H), 7.55-7.66 (m, 3H), 7.72(s, 1H).

EXPERIMENTAL EXAMPLE 1. Yield Evaluation Depending on the Reaction Solvent in the Synthesis of 1-chloro-6-(3-chloro-1-isopropyl-1H-indazol-5-ylmethoxy)-3,4-dihydro-naphthalene-2-carbaldehyde In the synthesis reaction of Example 1, the yield and the purity of the reaction product depending on the reaction solvent were evaluated. The evaluation results are shown in Tables 1 and 2, respectively.

In Tables 1 and 2, "SG40" refers to "1-chloro-6-(3-chloro-1-isopropyl-1H-indazol-5-ylmethoxy)-3,4-dihydro-naphthalene-2-carbaldehyde."

TABLE 1

| Entry | Reaction solvent | Reaction time (hour) | HPLC (PAR %) RT15 min Dimer IMP. | SG40 |
|---|---|---|---|---|
| 1 | DMF | 5 | 2.61 | 97.39 |
| | | 16 | 5.23 | 94.77 |
| 2 | DMA | 5 | 0.37 | 99.63 |
| | | 16 | 0.42 | 99.58 |

TABLE 2

| SG40 | HPLC (PAR %) | | SG40 | HPLC (PAR %) | |
|---|---|---|---|---|---|
| Batch with DMF solvent | RRT 0.88 | 0.06 | Batch with DMA solvent | RRT 0.88 | 0.02 |
| | N2 isomer | 0.04 | | N2 isomer | 0.05 |
| | RT15.0 | 4.90 | | RT15.0 | 0.13 |
| | RRT 1.44 | 0.27 | | RRT 1.44 | 0.28 |
| | Purity | 84.57 | | Purity | 86.97 |

As shown in Table 1, it was confirmed that in the synthesis reaction in DMF, the impurity content was increased from 2.6% to 5.3%, whereas in the synthesis reaction in DMA, the impurity content was 0.4%, and thus the generation of the impurity was inhibited.

In addition, as shown in Table 2, it was confirmed that the purity of the product obtained using the DMA solvent in the synthesis reaction could also be improved.

Meanwhile, the result of evaluating the degree of impurity removal through washing after performing the synthesis reaction in the DMF reaction solvent as described above is shown in Table 3 below.

TABLE 3

| W/U washing (number of times) | W/U after DMF reaction Layer | HPLC (PAR %) RT15 min Dimer IMP. | SG40 |
|---|---|---|---|
| 1 | DCM | 4.91 | 95.09 |
| | $H_2O$ | 38.45 | 61.55 |
| 2 | DCM | 4.76 | 95.24 |
| | $H_2O$ | 99.18 | 0.82 |
| 3 | DCM | 4.58 | 95.42 |
| | $H_2O$ | 77.87 | 22.13 |

As shown in Table 3, when the synthesis reaction was performed in the DMF solvent, the impurity content was reduced from 4.91% to only 4.58% even after washing the reaction product three times. Thus, it was confirmed that the impurity could not be removed easily through washing.

Accordingly, it was confirmed that it is preferable to use DMA as the reaction solvent in terms of the yield and purity of the product during the synthesis reaction.

EXPERIMENTAL EXAMPLE 2. Evaluation of Crystallization Conditions for 1-[1-chloro-6-(3-chloro-1-isopropyl-1H-indazol-5-ylmethoxy)-3,4-dihydro-naphthalen-2-ylmethyl]-piperidine-4-carboxylic acid hydrochloride To reduce the impurities of the finally prepared 1-[1-chloro-6-(3-chloro-1-isopropyl-1H-indazol-5-ylmethoxy)-3,4-dihydro-naphthalen-2-ylmethyl]-piperidine-4-carboxylic acid hydrochloride to 0.10% or less and control the residual amount of the DMC solvent limitingly to 600 ppm, the crystallization conditions were evaluated.

Evaluation of Crystallization Solvents

The product yield and purity were evaluated when the amount of DCM used during crystallization was increased from 0.1-fold to 0.5-fold, and the result is shown in Table 4 below. The result of measuring the residual solvent in the product is shown in Table 5.

In Tables 4 and 5 below, "SG50" refers to "1-[1-chloro-6-(3-chloro-1-isopropyl-1H-indazol-5-ylmethoxy)-3,4-dihydro-naphthalen-2-ylmethyl]-piperidine-4-carboxylic acid hydrochloride."

As shown in Table 4, it was confirmed that similar levels of yield and purity were obtained when the amount of DCM used was increased. As shown in Table 5, it was confirmed that when 0.1-fold of DCM was used, it remained at a 400 ppm level, while 0.2-fold was used, it remained at a 800 ppm level.

Accordingly, 0.1-fold or less of DCM should be used. But in Table 4, there was no significant difference in terms of purity when DCM was not used, and thus it was confirmed that it might be preferable to perform crystallization without using DCM.

TABLE 4

| | | Addition | HPLC (Area %) | | | | | | |
|---|---|---|---|---|---|---|---|---|---|
| | temp. | time | RRT | | | | | — | Yield |
| Solvent | (° C.) | (min) | 0.88 | 0.91 | SG70 | 1.39 | 1.44 | SG50 | (%) |
| SM (Starting material) | | | 0.135 | 0.039 | 99.050 | 0.085 | 0.095 | 0.031 | — |
| IPOAc 2.0-fold<br>EtOH 3.0-fold<br>Water 5.0-fold | 20-25 | 120 | 0.135 | 0.032 | 99.299 | 0.079 | 0.059 | 0.019 | 85 |
| DCM 0.1-foldIPOAc 2.0-fold<br>EtOH 3.0-fold<br>Water 5.0-fold | 20-25 | 120 | 0.141 | 0.032 | 99.286 | 0.081 | 0.055 | 0.014 | 83.5 |
| DCM 0.2-foldIPOAc 2.0-fold<br>EtOH 3.0-fold<br>Water 5.0-fold | 20-25 | 120 | 0.149 | 0.044 | 99.251 | 0.083 | 0.058 | 0.011 | 87 |
| DCM 0.3-foldIPOAc 2.0-fold<br>EtOH 3.0-fold<br>Water 5.0-fold | 20-25 | 120 | 0.145 | 0.047 | 99.254 | 0.085 | 0.051 | 0.017 | 84.5 |
| DCM 0.5-foldIPOAc 2.0-fold<br>EtOH 3.0-fold<br>Water 5.0-fold | 20-25 | 120 | 0.155 | 0.026 | 99.287 | 0.082 | 0.055 | 0.015 | 88.5 |

TABLE 5

| Solvent | temp. (° C.) | Addition time (min) | Residual solvent (NMR %) | | |
|---|---|---|---|---|---|
| SM | | | DCM | EtOH | EtOAc |
| IPOAc 2.0-fold<br>EtOH 3.0-fold<br>Water 5.0-fold | 20-25 | 120 | — | 0.31 | 0.37 |
| DCM 0.1-foldIPOAc 2.0-fold<br>EtOH 3.0-fold<br>Water 5.0-fold | 20-25 | 120 | 0.04 | 0.28 | 0.33 |
| DCM 0.2-foldIPOAc 2.0-fold<br>EtOH 3.0-fold<br>Water 5.0-fold | 20-25 | 120 | 0.08 | 0.22 | 0.25 |
| DCM 0.3-foldIPOAc 2.0-fold<br>EtOH 3.0-fold<br>Water 5.0-fold | 20-25 | 120 | 0.13 | 0.21 | 0.23 |

Evaluation of Time Required for Dropwise Addition of Hydrochloric Acid

The shape of the particles depending on the time for hydrochloric acid was added in the crystallization process was confirmed. The crystals produced by adding hydrochloric acid for 10 to 60 minutes were compared. In Easymax, it was confirmed that the uniform shape of the particles was obtained when hydrochloric acid was added dropwise for 30 minutes at a stirring speed of 500 rpm (FIG. 1).

Evaluation of Hydrochloric Acid Dropwise Addition Temperature

The purity and yield of the reaction product and the residual solvent were evaluated by varying the temperature at which hydrochloric acid was added, and the results are shown in Tables 6 and 7 below, respectively.

In Table 6, "SG70" refers to "1-[1-chloro-6-(3-chloro-1-isopropyl-1H-indazol-5-ylmethoxy)-3,4-dihydro-naphthalene-2-ylmethyl]-piperidine-4-carboxylic acid hydrochloride crystals."

TABLE 6

| Solvent | Hydrochloric acid additionon temperature (° C.) | Hydrochloric acid addition time (min) | Aging temperature (° C.) | Purity (%) | Yield (%) | HPLC (Area %) 0.89 13.9' | 0.91 13.9' | 0.98 14.5' | SG70 14.7' | behind SG70 14.9' | 1.39 15.6' | 1.44 16.5' |
|---|---|---|---|---|---|---|---|---|---|---|---|---|
| | | SM | | | | 0.142 | 0.108 | 0.023 | 98.933 | 0.092 | 0.088 | 0.103 |
| IPOAc 2.0-fold EtOH 2.0-fold Water 5.0-fold | 25 | 30 | 25 | 99.174 | 87.6 | 0.142 | 0.087 | 0.015 | 99.174 | 0.077 | 0.075 | 0.068 |
| IPOAc 2.0-foldEtOH 2.0-fold Water 5.0-fold | 20 | 30 | 20 | 99.066 | 91.0 | 0.147 | 0.085 | 0.026 | 99.066 | 0.082 | 0.067 | 0.070 |
| IPOAc 2.0-foldEtOH 2.0-fold Water 5.0-fold | 10 | 30 | 10 | 98.997 | 88.3 | 0.148 | 0.098 | 0.023 | 98.997 | 0.085 | 0.092 | 0.084 |
| IPOAc 2.0-foldEtOH 2.0-fold Water 5.0-fold | 5 | 30 | 5 | 98.892 | 95.6 | 0.144 | 0.090 | 0.015 | 99.130 | 0.072 | 0.078 | 0.080 |
| IPOAc 2.0-foldEtOH 2.0-fold Water 5.0-fold | 25 | 60 | 25 | 99.167 | 84.3 | 0.152 | 0.076 | 0.022 | 99.154 | 0.076 | 0.071 | 0.065 |
| IPOAc 2.0-foldEtOH 2.0-fold Water 5.0-fold | 5 | 60 | 5 | 99.091 | 93.6 | 0.145 | 0.093 | 0.016 | 99.096 | 0.070 | 0.080 | 0.089 |
| IPOAc 2.0-foldEtOH 2.0-fold Water 5.0-fold | 25 | 10 | 25 | 99.065 | 89.3 | 0.139 | 0.088 | 0.025 | 99.087 | 0.075 | 0.074 | 0.067 |
| IPOAc 2.0-foldEtOH 2.0-fold Water 5.0-fold | 5 | 10 | 5 | 98.969 | 91.3 | 0.149 | 0.096 | 0.024 | 98.992 | 0.074 | 0.092 | 0.089 |

TABLE 7

| Solvent | Hydrochloric acid addition temperature (° C.) | Hydrochloric acid addition time (min) | Aging temperature (° C.) | Purity (%) | Yield (%) | Residual solvent IPOAc (%) | EtOH (%) |
|---|---|---|---|---|---|---|---|
| IPOAc 2.0-fold EtOH 2.0-fold Water 5.0-fold | 25 | 30 | 25 | 99.174 | 87.6 | 0.37 | 0.23 |
| IPOAc 2.0-foldEtOH 2.0-fold Water 5.0-fold | 20 | 30 | 20 | 99.066 | 91.0 | 0.52 | 0.29 |
| IPOAc 2.0-foldEtOH 2.0-fold Water 5.0-fold | 10 | 30 | 10 | 98.997 | 88.3 | 0.96 | 0.48 |
| IPOAc 2.0-foldEtOH 2.0-fold Water 5.0-fold | 5 | 30 | 5 | 98.892 | 95.6 | 1.31 | 0.61 |
| IPOAc 2.0-foldEtOH 2.0-fold Water 5.0-fold | 25 | 60 | 25 | 99.167 | 84.3 | 0.35 | 0.23 |
| IPOAc 2.0-foldEtOH 2.0-fold Water 5.0-fold | 5 | 60 | 5 | 99.091 | 93.6 | 1.27 | 0.62 |
| IPOAc 2.0-foldEtOH 2.0-fold Water 5.0-fold | 25 | 10 | 25 | 99.065 | 89.3 | 0.41 | 0.23 |
| IPOAc 2.0-foldEtOH 2.0-fold Water 5.0-fold | 5 | 10 | 5 | 98.969 | 91.3 | 1.21 | 0.56 |

The above results confirmed that when adding hydrochloric acid dropwise, it is preferable in terms of purity and yield of the product that the internal temperature in the reactor is 20-25° C.

Evaluation of Stirring Speed

Figure 2:
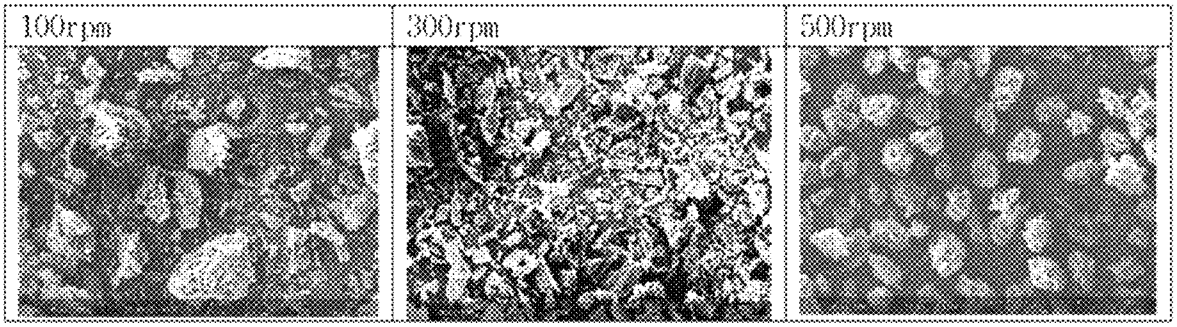
FIG. 2 is the SEM photograph of crystals generated when the stirring speed is changed during crystallization according to Experimental Example 2.

The effect of the stirring speed during the crystallization process was determined. Stirring speeds of 100 to 500 rpm were compared in Easymax. When the stirring speed was low, the produced crystals were precipitated at the bottom of the crystallizer. For this reason, when the stirring speed was low and thus the stirring was not smoothly carried out, it was confirmed that ununiform crystals were produced (FIG. 2).

The invention claimed is:

1. A method for preparing a compound of Formula 7 below or a salt thereof, comprising:

1) a step for preparing a compound of Formula 4 by coupling a compound of Formula 2 with a compound of Formula 3 in the presence of a dimethylacetamide (DMA) solvent;

2) a step for reacting the compound of Formula 4 and a compound of Formula 5 under a reducing condition to prepare a compound of Formula 6 or a salt thereof; and 3) a step for converting an ester group of the compound of Formula 6 or the salt thereof to a carboxylic acid group to prepare a compound of Formula 7 or a salt thereof:

[Formula 2]

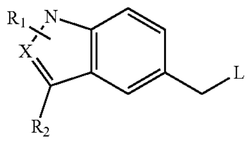

[Formula 3]

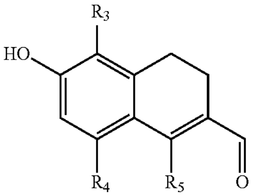

[Formula 4]

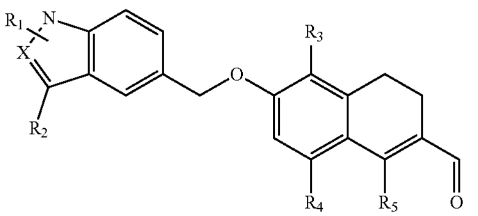

[Formula 5]

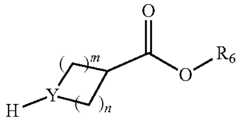

-continued

[Formula 6]

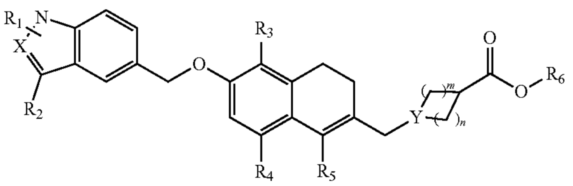

[Formula 7]

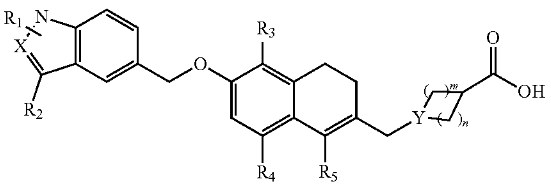

wherein

R1 is hydrogen or a substituted or unsubstituted alkyl,

R2 is hydrogen, a substituted or unsubstituted alkyl, a halogen, CN, $CF_3$, or $COCF_3$, R3 and R4 are each hydrogen, a substituted or unsubstituted alkyl, or a halogen, R5 is hydrogen, a substituted or unsubstituted alkyl, or a halogen, R6 is a substituted or unsubstituted alkyl, X is C or N, Y is N, O, or S, L is a leaving group, and m and n are each 0, 1, 2, or 3, and m+n>0.

2. The preparation method of claim 1, wherein R1 is a $C_1$-$C_4$ substituted or unsubstituted alkyl, R2 is a halogen, R3 and R4 are each hydrogen or a $C_1$-$C_4$ substituted or unsubstituted alkyl, R5 is a halogen, R6 is a $C_1$-$C_4$ substituted or unsubstituted alkyl, X is N, Y is N, and L is a leaving group selected from chlorine (Cl), bromine (Br), iodine (I), methanesulfonate (Oms), p-toluenesulfonate (OTs), and trifluoromethanesulfonate (OTf).

3. The preparation method of claim 1, further comprising 4) a step for recrystallizing the compound of Formula 7 or the salt thereof under an acidic condition.

4. The preparation method of claim 3, wherein the content of a dichloromethane (DCM) solvent in a fraction containing the recrystallized compound of Formula 7 or the salt thereof is 600 ppm or less.

5. The preparation method of claim 3, wherein a solvent for recrystallization includes water, an ester solvent, an alcohol solvent, or a mixed solvent thereof.

6. The preparation method of claim 5, wherein the solvent for recrystallization includes water, isopropyl acetate, and ethanol.

7. The preparation method of claim 3, wherein the recrystallization step comprises adding an acid compound at a temperature of 0-25° C.

8. The preparation method of claim 3, wherein the recrystallization step comprises stirring at a speed of 100 to 500 rpm.

9. The preparation method of claim 7, wherein the acid compound is added dropwise for 100 minutes.

* * * * *